(12) United States Patent
Rothman

(10) Patent No.: US 8,080,258 B2
(45) Date of Patent: Dec. 20, 2011

(54) ANTIMICROBIAL AGENT

(75) Inventor: Ulf Rothman, Channel Island (GB)

(73) Assignee: Svenska Miljobolaget SVV AB, Stockholm (SE)

( * ) Notice: Subject to any disclaimer, the term of this patent is extended or adjusted under 35 U.S.C. 154(b) by 298 days.

(21) Appl. No.: 10/231,400

(22) Filed: Aug. 29, 2002

(65) Prior Publication Data

US 2003/0124111 A1   Jul. 3, 2003

(30) Foreign Application Priority Data

Aug. 29, 2001   (SE) ...................................... 0102864

(51) Int. Cl.
*A01N 25/34* (2006.01)
*A61K 36/00* (2006.01)
*A61K 38/16* (2006.01)

(52) U.S. Cl. ........ 424/404; 424/776; 424/750; 424/757; 424/727; 530/358

(58) Field of Classification Search ........................ None
See application file for complete search history.

(56) References Cited

U.S. PATENT DOCUMENTS

| | | | | |
|---|---|---|---|---|
| 5,573,801 | A | * | 11/1996 | Wilhoit |
| 6,350,738 | B1 | * | 2/2002 | Savage et al. |
| 2001/0010909 | A1 | * | 8/2001 | Cahoon et al. |

FOREIGN PATENT DOCUMENTS

| | | |
|---|---|---|
| JP | 61-30526 | 2/1986 |
| JP | 61-030526 | 2/1986 |
| JP | 63-179899 | 5/1987 |
| JP | 62-116600 | 7/1988 |
| JP | 2000-7699 | 1/2000 |
| WO | WO 01/10901 A1 * | 2/2001 |
| WO | WO 01/010901 A3 | 2/2001 |
| WO | WO 0110901 A2 * | 2/2001 |

OTHER PUBLICATIONS

Gotay, IC et al. Proc. Soc. Exp. Biol Med. (1966); 122(4): 1115-1116. Differentiation of atypical *Pseudomonas aeruginosa* from *Alcaligenes fecalis* using a histone-like fraction from Carica papaya seeds.*
Hadwiger, LA et al. Phytopathology (1977); 67(6): 755-758. An evaluation of pea histones as disease resistance factors.*
Fambrough, DM et al. Biochemistry (1966): 5(8):n2563-70. On the similarity of plant and animal histones.*
Singh, NP et al. Plant Molecular Biology (1992): 33(3): 124-128. Nuclear proteins and chromatin structure of pea root nodule.*
Mitheiux, G et al. Biochemica et Biophysica Acta (1984); 781(3): 286-293. Study of chromatin domain different from bulk chromatin in barley Hordium-vulgare nuclei.*
Hoffmann, KL et al. J of Food Protection (Jun. 2001); 64(6): 885-889. Antimicrobial effects of corn zein films impregnated with nisin, lauric acid and EDTA.*
Esen, A. Plant Physiol (1986); 80: 623-627. Separation of alcohol-soluble proteins (zeins) from maize into three fractions by differential solubiltiy.*
Viotti, A et al. Molec Gen Genet. (1080): 178: 35-41. Chromosomal localization of zein genes by in situ hybridization in Zea mays.*
Spiker, S. "An Evolutionary Comparison of Plant Histones," Biochimica et Biophysica Acta (1975) 400: 461-467.
Hirsch, James G. "Bactericidal Action of Histone," J. Exp. Med. (1958) 108(6): 925-944.
Hancock, R. E. W. And Chapple, D.S. "Minireview: Peptide Antibiotics," Antimicrobial Agents and Chemotherapy (1999) 43(6): 1317-1323.
Hancock, R.E.W. "Peptide Antibiotics," Lancet (1997) 349: 418-422.
Cammue, B.P. et al., "Gene-encoded Antimicrobial Peptides from Plants", Ciba Foundation Symposium, 1994, vol. 186 pp. 91-106.
Esen, A., "Separation of alcohol-soluble proteins (zeins) from maize into three fractions by differential solubility", Plant Physiol, 1986, vol. 80, pp. 623-627.
Fambrough, D.M. and Bonner, J., "On the Similarity of Plant and Animal Histones", Biochemistry, 1966, 5(8):2563-2570.
Gotay, I.C., "Differentiation of Atypical *Pseudomonas aeruginosa* from *Alcaligenes fecalis* Using a Histone-Like Fraction from *Carica papaya* Seeds", Proc. Soc. Exp. Biol. Med., 1966, 122(4):1115-1116.
Hadwiger, L..A., "An Evaluation of Pea Histones as Disease Resistance Factors", Phytopathology, 1977, 67(6):755-758.
Hoffman, K.L. et al., "Antimicrobial Effects of Corn Zein Films Impregnated with Nisin, Lauric Acid, and EDTA", Journal of Food Protection, 2001, 64(6):885-889.
Viotti, A. et al., "Chromosomal Localization of Zein Genes by in situ Hybridization in Zea mays", Moled. Gen. Genet., 1980, 178:35-41.
Ye, X.Y. and Ng, T.B., "Mungin, a Novel Cyclophilin-like Antifungal Protein from the Mung Bean", Biochemical and Biophysical Research Communications, 2000, 276(3):1111-1115.
X.Y. Ye et al., "Mungin, a Novel Cyclophilin-Like Antifungal Protein From the Mung Bean," Department of Biochemistry, Chinese University of Hong Kong, Jun. 13, 2000, p. 2.

* cited by examiner

*Primary Examiner* — Michele Flood

(74) *Attorney, Agent, or Firm* — Fitzpatrick, Cella, Harper & Scinto

(57) ABSTRACT

A proteineous component isolated from plant chromatin, after dissociation of the same, as an antimicrobial agent, the proteineous component having an apparent molecular weight between 10 and 20 kD. The proteineous plant component is produced by means of a method comprising the steps of homogenizing a plant material in order to expose its plant chromatin, dissociating the plant chromatin with a dissociating agent under hydrophobic conditions, and separating the dissociated plant chromatin into individual fractions, one comprising the proteineous plant component, by means of a hydrophobic interaction separation procedure.

12 Claims, No Drawings

ANTIMICROBIAL AGENT

BACKGROUND OF THE INVENTION

1. Field of the Invention

The present invention relates to the use of a proteineous component isolated from plant chromatin. More precisely, the invention relates to the use of a proteineous component isolated from plant chromatin, after dissociation of the same, as an antimicrobial agent, as well as a method of producing the same.

2. Related Background Art

Most eukaryotic organisms produce a wide variety of protective mechanisms directed towards infectious agents. Several mechanisms are based on those fundamental differences, which exist in membrane composition and organization between microbes and cells of complex multicellular organisms, i.e. they are directed towards outer membranes of sensitive microbes. These membranes are composed of lipids having negatively charged head groups facing outwards, and the microbes apparently find it difficult to counteract the effects by altering their membrane composition and organization. Thus, the substances responsible for the antibiotic action are presumable candidates as substitutes for antibiotics.

One example is the phospholipid transfer proteins, which are able to transfer phospholipids between membranes. Antimicrobial phospholipid transfer proteins have been reported from a range of plant species including cereals, and these proteins vary in their activity against different pathogens. For example, in U.S. Pat. No. 5,698,200 it is shown that a plant part can be protected from a plant pathogenic bacterium by means of an aqueous extract obtained from malted cereal grain.

However, the most studied class of protective agents is the antimicrobial peptides. They are found in all species of life, ranging from plants and insects to animals, including molluscs, crustaceans, amphibians, birds, fish, mammals, and humans.

These peptides interact directly with bacteria and kill them. They are termed antimicrobial because they have unusually broad spectra of activity including the ability to kill or neutralize Gram-negative and Gram-positive bacteria fungi (including yeast), parasites (including planaria and nematodes), cancer cells, and even enveloped viruses like HIV and herpes simplex virus. In general, these agents range in length from as few as 12 amino acids to molecules with over 70 residues. More than 500 such peptides have been discovered.

The mode of antimicrobial action of the almost always cationic antimicrobial peptides has been studied in detail among such peptides as melittin, magainin, gramicidin, cecropin, and defensins. The antimicrobial molecules also generally damage the membranes of the organisms that they attack. The cationic antimicrobial peptides have been found to possess bactericidal activity in vitro as well as in vivo. They kill very rapidly, do not easily select resistant mutants, are synergistic with conventional antibiotics, is other peptides as well as lysozyme, and are able to kill bacteria in animal models.

As a consequence, antimicrobial peptides of animal origin are now developed as new antibiotic drug. Examples are the synthetic version of magainin (pexiganan) and the analogue of a protegrin, an antimicrobial peptide initially isolated from pig neutrophils.

However, natural sources have not proved to be economically profitable for the production of new alternative antibiotics. The only exception is the antimicrobial peptide nisin, which can be effectively produced in a *Lactococcus lactis* strain with high resistance to the substance.

An increasing number of larger proteins or fragments thereof have also been found to exhibit antimicrobial activities. For example, a murine macrophage protein, ubiquicidin, appears to be the same as the ribosomal protein S30. Also, two of the antimicrobial peptides in the stomach of bullfrog (*Rana catesbeina*) are derived from the N-terminus of pepsinogen. Likewise, an antimicrobial peptide, named buforin I, has been isolated from stomach tissue of an Asian toad (BBRC 218: 408, 1996). The amino acid sequence of the 39 amino acid long peptide was found to be identical with 37 of the 39 amino-terminal residues of the *Xenopus* histone H2A.

In addition, the whole protein molecule can exhibit an antimicrobial potential. Antimicrobial activity has been detected in acid extracts of liver, intestine, and stomach of atlantic salmons (BBRC 284:549, 2001): The corresponding antimicrobial protein can be isolated from salmon liver using acid extraction followed by ammonium sulfate precipitation, large-scale gel chromatography (gel filtration), reverse-phase HPLC, and size exclusion HPLC. The salmon antimicrobial (SAM) protein was found to have a molecular mass of 27.7 kD and was identified as the histone H1 protein. In WO 200110901, the mammalian histone H1 protein from bovine thymus is used in antimicrobial compositions for treating microbial infections in different eucaryotic organisms. Thus, proteins having other well-established functions appear to exhibit a second property by being antimicrobial.

However, the use of bovine proteins, especially proteins from bovine thymus, should be avoided since such a material can be contaminated with deleterious virus, especially hepatitic viruses, or other pathogenic agents, for example priones. Bovine material—whether contaminated or not—must be subjected to extremely strict tests when intended to be used in connection with humans.

Furthermore, the isolation of new alternative antibiotics involves the collection of specified animal organs or tissue, followed by complex purification procedures in order to obtain a product that can be used in connection with human beings or domestic animals.

SUMMARY OF THE INVENTION

The purpose of the invention is to provide a new antimicrobial agent, whereby the above-mentioned problems are eliminated.

Another purpose of the invention is to provide an antimicrobial agent, whereby the risk is avoided of passing on infectious agents pathogenic to man and/or animals.

Still another purpose is to provide an antimicrobial agent which is tasteless when used in connection with food.

A further purpose of the invention is to provide a method of producing an antimicrobial agent, in which cheap starting materials are utilized.

Yet a further purpose is to provide a method of producing an antimicrobial agent in a practically unlimited scale.

Still yet a further purpose is to provide a method of producing an antimicrobial agent, which does not require investments manufacturing in plants for bacterial fermentation.

These objects are accomplished by the use as well as the method according to the invention as claimed.

According to the invention a method is provided which in a simple and rational way allows for the production of a proteineous component which can be used as an antimicrobial product, for example as a drug, a full preserving agent during manufacturing and transport, a functional food and/or neutraceutical additive as well as an animal feed additive.

DETAILED DESCRIPTION OF THE INVENTION

A proteineous component can be prepared with surprisingly ease from an initially inert starting material comprising plant chromatin. In the inventive method, DNA is separated from basic nuclear plant chromatin. Preferably, the plant chromatin is obtained from plant seeds. Suitable plant seeds are obtained from oats, grain sorghum, milo, wheat, barley, rye, corn, rice, rape, soy, millet, or buckwheat. However, any chromatin containing plant material, such as seaweed and other marine plants, can be used for the preparation of an antimicrobial proteineous component on a large scale.

The plant chromatin used for the isolation of the proteineous component should be a heterochromatin (silent chromatin or "junk" DNA. The heterochromatin is hypoacetylated (deacetylated) chromatin, which assumes a more condensed structure than hyperacetylated chromatin due to a higher electropositive charge.

In addition, the choice of chromatin starting material for further specific protein extraction is also dependent on plant cell tissue location and state of differentiation. For example, a tissue comprised of small cells will have a higher cell density, and therefore is likely to contain more nucleic acids and accompanying antibacterial proteineous component than another same amount of tissue comprising larger cell size.

Likewise, many plants carries very large basal genome sizes due to high heterochromatin content, further enhanced by a polyploidy possibility. In this connection the amount of DNA per haploid cell as measured in the number of base pairs (the c-value) is referred to. The variation in DNA content of an organism is reflected by its DNA c-value or basal genome size. The c-value is defined as the content of DNA as measured by weight or number of base pairs in a single copy of the entire sequence of DNA found within cells of that organism. It is the amount of nuclear DNA in its unreplicated haploid or gametic nucleus, irrespective of the ploidy level of the taxon. Thus, the c-value equals the genome size in diploid species, but always exceeds genome size in polyploid species.

It is also preferred that self-renewing undifferentiated stem cells of plants are utilized These are found in meristems, regions that provide new growth at shoot and root tips. Thus, plant seedling root-tips are the superior starting material for chromatin extraction and subsequent downstream isolation of the proteineous component according to the invention. Such raw material is readily available in unlimited quantities, as being a waste product during the manufacturing of brewery malt and wheat germ oil.

Other plant raw materials of mitotically dividing cells under optimal growing conditions are also suitable for the preparation of a proteineous component according to the invention. Any germinating sprouts and rootlets or germs in germination phase can be used. Preferably, seeds of one of the four kinds of corn is used, which are allowed to germinate.

A cost effective raw material to be used according to the present invention is what is called green malt, which is a starting material for beer production. The brewery industry produces green malt from barley, which after moisturizing is allowed to germinate for six days (malting). This industrially produced green malt, or by-products thereof (rootlings), can according to the invention be used for the production of an antimicrobial proteineous component.

Accordingly, rootlings of diploid corn and barley (DNA c-value of 5,000 Mbp) as well as onion (DNA c-value of 18,000 Mbp) are suitable starting extraction materials. Preferably, the antibacterial proteineous component is extracted from a chromatin source, the DNA c-value of which exceeds 3,000 Mbp.

It is especially preferred that the starting material of the purification procedure comprises plant chromatin isolated from proliferating plant cells in S-phase. Germinating seeds (grains) with their rootlings as well as young leaves thus contain a large number of cells in S-phase.

In the inventive method of producing a proteineous plant component having antimicrobial activity, the method comprises the steps of
  homogenizing a plant material in order to expose its plant chromatin;
  dissociating the plant chromatin with a dissociating agent under hydrophobic conditions; and
  separating the dissociated plant chromatin into individual fractions, one comprising the proteineous plant component, by means of a hydrophobic interaction separation procedure.

Accordingly, the plant material is first homogenized. In this connection the term homogenization means a disruption of the plant material cell walls in such a way that the chromatin of the plant is exposed and a homogenate is obtained as a slurry. The cell walls may be disrupted by any of a number of methods known to those skilled in the art including, but not limited to, high shear mixing, sonication, mechanichal disruption, explosion by pressure etc. The cell walls are disrupted by means of a suitable device, whereby a homogenate is obtained.

The plant chromatin in the homogenate is then dissociated by means of a dissociating agent in an aqueous solution thereof under hydrophobic conditions. Such conditions are those which promote hydrophobic interactions.

Suitable dissociating agents are urea, guanidinium chloride, and a chloride salt. Preferably, the chloride salt is sodium chloride of high ionic strength.

It is an advantage if the homogenizing of the plant material is performed in the dissociating agent. In this way the purification procedure is simplified and the number purification steps are reduced.

The purification procedure of green malt is commenced by the homogenisation of the malt in an almost saturated salt solution comprising 4 M sodium chloride. The high ionic strength dissociates the chromatin as well as nucleosomes, a simultaneous degradation of proteineous material by proteases at the same time being prevented. Preferably, the homogenisation is performed in the presence of a hydrophobic matrix.

The homogenate can then sieved on a sieve or a wire net or the like in order to remove cell debris or other particles from the plant chromatin, which are retained thereon. In this way a clear solution is obtained that facilitates a subsequent purification of the dissociated plant chromatin.

The dissociated plant chromatin is then separated into individual fractions, one comprising the proteineous plant component having antimicrobial activity. The separation is preferably performed by means of a hydrophobic interaction separation procedure. Preferably, the hydrophobic interaction separation procedure is hydrophobic chromatography.

Other examples of suitable separation procedures are partition in polymeric systems, such as partition chromatography, counter current distribution, and gas aphron partition. The separation of the dissociated chromatin components can alternatively be performed on columns with metal chelate gels or immobilized heparin.

The functional ligand of the matrix used for the hydrophobic interaction and/or separation procedure should be an ether, an isopropyl, a butyl, or an octyl group. A phenyl group should be avoided. Preferably, the functional ligand is a butyl group on an agarose matrix which is cross linked to 4%. A ligand density of 40-50 μmol/ml is the achieved, which results in a binding capacity of 7 mg IgG per ml.

For example, after screening of the green malt homogenate as a slurry, a hydrophobic matrix is added batchwise to the solution obtained, the hydrophobic matrix being an hydrophobic interaction chromatography gel (HIC) containing active butyl groups. Suitable matrixes are Novarose® S-Butyl 1000/40 from Inovata AB, Bromma, Sweden, and Butyl Sepharose® 4 from Amersham Pharmacia Biotech, Sweden. The hydrophobic matrix is then washed with the high ionic strength salt solution, DNA being washed out.

Then the matrix is poured into a column and subjected to a stepwise gradient elution with decreasing ionic strength of sodium chloride. A distinct antimicrobial proteineous component is eluted at a concentration of 1 M NaCl.

The proteineous component can be further purified by means of a conventional method suitable for purification of peptides/proteins. Such methods include centrifugation, precipitation at the isoelectric point, phase separations, ultrafiltration, gel chromatography (size exclusion chromatography), ion exchange chromatography or HPLC, as well as a combination of such methods. Preferably, the subsequent separation procedure is gel chromatography or ion exchange chromatography.

Most preferably, a preparative gel chromatography step is accomplished in a column packed with a gel having an exclusion limit of 100 kD. The column is equilibrated with distilled water before being loaded with the fraction of 1 M NaCl exhibiting antibiotic activity. The column is then eluted with distilled water or ammonium acetate. In this way a desalting and purification is obtained at the same time in one and the same step. Thus, the proteineous component can be concentrated to dryness, for example by means of lyophilization, without any further purification steps.

A protein fraction having an apparent molecular weight between 10 and 20 kD was isolated, which exhibited antimicrobial properties.

It will be appreciated by the skilled man within the art that the purification of the proteineous component may be accomplished by many other methods known to those skilled in the art, all of which are contemplated by this invention.

A complexing agent, such as heparin, alginic acid, phytic acid, or a vanadinium compound, can also be used as a dissociating agent, provided that it dissociates the plant chromatin into its individual components Alginic acid is especially preferred as a dissociating agent, alginate complexes with the antibiotically active proteineous component being formed. Such complexes can be used with the aim of purification or be used as such for slow release of antimicrobial activity therefrom.

Before the separation of the dissociated plant chromatin into individual fractions according to the invention by means of for example a hydrophobic interaction separation procedure, no antimicrobial activity at all could be found in the starting material of dissociated chromatin. When proteineous plant components are purified according to the invention, the heterochromatin will automatically be utilized. Thus, the biological activity is successively formed by the physical separation of chromatin components. Theoretically, the separation procedure could result in an altered molecular structure of the components.

It is generally accepted that antimicrobial peptides exercise their action on prokaryotes by positive charge. The very likely action mechanisms of the proteineous component obtained according to the invention is not expected to differ from what is known about other cationic polypeptides. However, known basic peptides would allow for an interaction with cell membranes which mimics that of detergents. Such an action mechanism of the proteineous component is confirmed by its activity directed against Gram-positive bacteria as well as Gram-negative bacteria.

According to the invention, other antimicrobially active proteineous components may be obtained from other plant materials by means of other purification procedures after the elution from the hydrophobic matrix This is due to the fact that proteins from different biological materials exhibit different post-synthetical modification patterns which reflect cellular activities of the plant material. Thus, a separation pattern should be influenced by the degree of for example acetylation, phosphorylation, methylation, ubiquitination, glycosylation, as well as ADP-ribosylation of a proteineous component obtained according to the invention.

Correspondingly, the isolated proteineous component from plant chromatin can subsequently be chemically modified. Such modifications include changes in molecular weight and/or acetylating level and would result in preparation forms having a more specific biological activity.

The antimicrobial effect of the proteineous component obtained by means of the inventive method can be determined in a standardized Bioscreen® method, nisin being used as a control substance. In comparison to nisin, an effect was obtained with the proteineous component corresponding to 2-4 mg/ml, the effect being cidal. Furthermore, an effect against Gram-negative bacteria was obtained, which is lacking with nisin.

The simple inventive purification method allows for the production of an antimicrobial proteineous component in a practically unlimited scale. The process yield is about 1 g protein from 1 kg of raw material (for example root-lings). By using germinating seeds with maximum protein synthesis the yield can be maximized, as is shown for example by malting for six days. When proliferating plant cells in S-phase are used, the natural chromatin protein synthesis is maximal and can represent up to 80% of the total protein synthesized.

The proteineous component isolated from plant chromatin according to the invention as an antimicrobial agent can be intensified together with one or more antimicrobially synergistic agents, Example of such antimicrobially synergistic agents are lysozyme, protamine, chelating agents, cupric compounds, and bacteriocins.

The plant chromatin proteinous component is suitable in the manufacturing of a pharmaceutical composition for treating microbial infections. The invention also refers to a method for treating microbial infections in mammals, including humans, whereby a therapeutically effective amount of the proteineous component is administered.

The proteineous component can be used in oral applications for treating dental and gum disorders, topical applications for use externally, such as dermatological disorders, skin and hair disorders, and oto-ophthalmologic disorders. The plant chromatin proteineous component can also be used in body cavities, such as mouth, throat, lungs, vagina, and rectum, as well as per oral for treatment of gastrointestinal disorders following digestion of pathogenic microorganisms.

When the proteineous component is to be used as an antimicrobial agent, it can be formulated in buffered aqueous media containing a variety of salts and buffers. Preferably, the salts are alkali and alkaline earth halides, e.g. sodium chloride, potassium chloride, or sodium sulphate. Various, such as buffers may be used, such as citrate, phosphate, HEPES, Tris or the like to the extent that such buffers are physiologically acceptable for its purpose.

Various excipients or other additives may be used, when the proteineous component is formulated as a lyophilized powder, for subsequent use in solution. The excipients may include various polyols, inert powders or other extenders.

The inventive use also includes a composition which comprises the purified proteineous component in an amount effective to kill bacteria or fungi and a suitable carrier. Such compositions may be used in numerous ways to combat bacteria and fungi, for example in household or laboratory antimicrobial formulations using carriers well-known in the art.

Different compositions will have different degrees of activities towards different organisms. Effective amounts to be used for killing harmful microorganismes, such as bacteria and fungi, and other noxious agents may be readily determined by those skilled in the art.

The proteineous component according to the present invention may also be combined with other proteins to act as preservatives in order to protect the proteineous component against proteolytic degradation. Alternatively, the inventive proteineous component or compositions may be used as preservatives or disinfectants in a wide variety of formulations, such as contact lens solutions, ointments, shampoos, medicaments, foods, and the like. The amount of proteineous component may vary depending upon the nature of other components, the degree of antimicrobial protection required, and the intended use of the composition.

The proteineous component can for example be used together with a suitable carrier in a composition for disinfection and cold sterilization of surfaces and as an adjuvant in food high-pressure pasteurization as well as in a composition as a water preservation agent, e.g. in pisciculture. The proteineous component can also be used in an amount effective to kill bacteria when enclosed in packaging materials to be slowly released therefrom.

EXAMPLES

The invention will now be further described and illustrated by reference to the following examples. It should be noted, however, that these examples should not be construed as limiting the invention in any way.

Example 1

Antibacterial Assay

The wells of a microtitre plate was filled with 300 μl growth medium (Nutrient Broth+1% glucose) at twice its concentration. Duplicate samples were added to final concentrations of proteineous components of 2, 0.5, and 0.2 mg/ml protein, respectively.

Two test organisms were used: *Pseudomonas fluorescens* (a Gram-negative aerobic bacterium) and *Listeria innocua* (a Gram-positive aerobic bacterium).

Overnight cultures of the bacterial strains were diluted in peptone water, and 50 μl of each strain was added to the wells at a concentration of $10^4$ cells/ml. Reference wells (positive controls) were used, which contained no test material.

The plates were incubated at 30° C. for 72 h in a Bioscreen® analyzing apparatus, the bacterial growth being registered as increased absorbency at visual light every $15^{th}$ minute.

Example 2

Extraction and Fractionation

When extracting and fractionating plant proteins and polypeptides the differences in the structure, physiology and biochemistry of plant tissues often do not allow for the application of current or conventional animal buffers and/or maceration techniques. The more complex macromolecular composition and interactions within plant tissues (e.g., phenolic, carbohydrate, and hydrocarbon compounds) as well as the more compact cell wall necessitate more stringent maceration and isolation methods in plant extract preparation to ensure the integrity of the polypeptides.

Barley leaves (1 kg, fresh weight) were subjected to the extraction and fractionation procedure of Langenbuch et al., Plant Molecular Biology 2, 207-220 (1983). Barley nuclei chromatin was obtained with 0.4 N sulphuric acid at a typical yield of 10-20 mg.

The special subfractionation technique was followed, which allows for large scale preparative isolation of proteineous components. A specific proteineous component (MW 17,300) was obtained by differential solubility in ethanol (80%):HCl (0.25 N).

The proteineous components were assayed for antimicrobial activity against the standard in house *Listeria* and *Pseudomonas* strains.

A total inhibition of the growth of both organisms was obtained with the fraction soluble in both ethanol and water. The effect is concentration dependent, i.e. a certain threshold value must be reached (no effect is obtained at the dilution 1:1).

The antimicrobial activity is exclusively restricted to the specific proteineous component of MW 17,300. No activity was obtained with a larger proteineous component.

Example 3

Alternative Extraction and Fractionation

Two-week-old pea, wheat, rye and cotton seedlings were subjected to the subfractionation procedure according to Sidorova & Konarev, Biokhimiia 46, 1298 (1981).

A specific proteineous component of MW 17,300 as well as a larger proteineous component was obtained.

The proteineous components were assayed for antimicrobial activity and the results were identical to those in Example 1.

Example 4

Improved Fractionation Procedure

Green malt was obtained from a local brewery. The malt had been germinated in a conventional malting process for 6 days.

The green malt (100 g) was suspended in 4 M NaCl and homogenized for about 10 minutes in a Braun mixer, The homogenate was filtered through a sieve of 20 μm, and the solution obtained then was added to 20 g of a hydrophobic matrix (Novarose® S-Butyl 1000/40 Inovata AB, Sweden) equilibrated in 4 M NaCl The mixture was agitated for 10 minutes and the matrix was filtered through a sieve of 40 μm.

Then the matrix was packed into a column (25×50 mm) and washed with 4 M NaCl before elution. At this high ionic strength, the DNA does not bind to the matrix, as determined by the increased absorbency of the eluate at 254 nm, and will thus be eluted during the procedures of packing and washing the column.

Distinct protein peaks were registered by means of UV absorption at 276 nm after stepwise elution with 2 M NaCl, 1 M NaCl, and water, respectively. This corresponds to a desorption at 2 M NaCl of non-chromatinic material.

Example 5

Subfractionation Procedure

The fraction desorbed at 1 M NaCl in Example 4 was further sub-fractionated by means of preparative gel chromatography in 0.1 M ammonium acetate on a column (25×500 mm) of Novarose® SE-100/40, (Inovata AB, Sweden).

Three protein fractions were obtained and lyophilized. The middle protein fraction had a retention volume which corresponds to a molecular weight between 10 and 20 kD.

Accordingly, plant chromatin is a convenient source for the isolation in this molecular weight range of hypoacetylated hydrophobic basic proteins having a high electropositive charge.

Upon analytical gel chromatography in 0.1 M phosphate buffer, pH 7.0, on a column (8×300 mm) of Novarose® SE100/17, (Inovata AB, Sweden), this fraction was found to correspond to a mean molecular weight of about 14 kD.

Example 6

Alternative Fractionation Procedure

A comparative experiment was performed with the same conditions as in Example 4 but with Novarose® S-Phenyl (Inovata AB, Sweden) as hydrophobic matrix. No protein desorption could be detected when the column was eluted with 1 M NaCl, and only one fraction was obtained after elution with water. Neither does a solution of 22% ethanol in water result in a desorption of proteineous material from the hydrophobic matrix, indicating that the binding between matrix and proteineous material is extremely hydrophobic.

Example 7

Establishment of Antimicrobial Activity

The middle fraction obtained according to Example 5 was further examined with reference to its antimicrobial activity. Samples were prepared by dissolving the lyophilized fraction in phosphate buffer (pH 7.0) to a concentration of 4 mg/ml. These solutions were then diluted four to ten times with the phosphate buffer.

The results obtained are inseparable to those obtained in Example 5 by the specific proteineous component of MW 17,300, when prepared according to the protocol of Example 4 and 5.

It should be noted that no other fraction from the gel chromatography procedure exhibited any antimicrobial activity at all.

Example 8

Effect of C-Value

Proteineous components of similar antimicrobial activity were isolated by the same procedure as described in Examples 4 and 5 from both 72 h arabidopsis and wheat seedling chromatins. The mean yields of the 10-20 kD middle fractions from these species are strikingly different, wheat being a far more favourable extraction source. Compared to barley, the desired fraction is present in approximately double amounts.

Example 9

Analytical Electrophoresis

Analytical electrophoresis following a standard protocol (Panyim & Chalkley, Biochem. 8:3972, 1969), display multiple variants of the specific proteineous component of MW 17,300 without the presence of any higher molecular weight subfractions of proteineous components of a molecular weight between 28,000 and 35,000.

These results also reflect the difference in genome size between plant species. Arabidopsis has a small 200 Mbp diploid genome and correspondingly lower yields than wheat which, has a large hexaploid genome of 17,000 Mbp.

Accordingly, the extraction yield is closely related to the size of the genome expressed as its c-value.

Comparative Example 1

Comparison with Animal Histones

Since the analytical chromatography in buffered separation media as in Example 5 resulted in a molecular weight of about 14 kD which corresponds to the molecular weights of the calf histones H2A and H2B, a comparison was performed between the proteineous component according to the invention and animal histones.

Parallel control experiments with commercially available calf histones H2A and H2B (Sigma, USA) and the middle fraction obtained in Example 4, having a molecular weight between 10 and 20 kD, were performed by means of analytical gel chromatography in 0.1 M phosphate buffer, pH 7.0, on a column (8×300 mm) of Novarose® SE-100/17, (Inovata AB, Sweden).

All fractions obtained were assayed for antibacterial activity, the positive results being repeated for the proteineous component isolated from plant chromatin.

Another comparative experiment did not prove any antimicrobial activity by the first fraction close to the void, a position expected for the plant histone H1. Furthermore, it is again established that the dissociation pattern of the nucleosomes in a salt solution differ between animals and plants, and a standard protocol used for animals can not be used for plants.

Comparative Example 2

Aqueous Solvent Extraction

Few methods are available, which allow for the extraction of whole plant tissue polypeptides. The methods used favor the preparation of fractions of various tissues, which are enriched with subcellular components. In contrast, a number of more or less "universal" preparative techniques have been described for animal systems.

Such techniques were studied by Karen Barrett, U.S. Pat. No. 5,698,200, several simple aqueous solvent extractions on malted cereal grain being examined.

The same downstream methods as disclosed in Example 1 and 2 of U.S. Pat. No. 5,698,200 were used with barley leaves (c.f. Example 2) as starting material.

Only storage proteins in the range of 10-20 kD were identified. These proteins do not exhibit any antibacterial activity at all.

It is concluded that no chromatin can be released by any methods described in U.S. Pat. No. 5,698,20, the starting material being cytosolic matter. Most likely, thionins were obtained, which are well-known plant defensins characterized as cytotoxic sulphur polypeptides of low molecular weight, 2-3 kD.

The invention claimed is:

1. A method of inhibiting the growth or killing bacterial microorganisms comprising treating the bacterial microorganisms with an effective amount of an antibacterial agent which is a protein fraction isolated from dissociated plant chromatin, the protein fraction having an apparent molecular weight between 10 and 20 kilodaltons (kD), wherein the bacterial microorganisms are Gram-positive bacteria or Gram-negative bacteria.

2. The method of claim 1, wherein the plant chromatin is heterochromatin.

3. The method of claim 1, wherein the plant chromatin has a deoxyribonucleic acid (DNA) c-value that exceeds 3,000 megabase pairs (Mbp).

4. The method of claim 1, wherein the plant chromatin is obtained from plant seeds.

5. The method of claim 4, wherein the plant seeds are obtained from oat, wheat, barley, rye, corn, rice, rape, soy, millet, or buckwheat.

6. The method of claim 4, wherein the plant chromatin is obtained from said the seeds during germination.

7. The method of claim 1, wherein the Gram-positive bacteria are *Listeria innocua*.

8. The method of claim 1, wherein the Gram-negative bacteria are *Pseudomonas fluorescens*.

9. The method of claim 1, wherein the protein fraction is in combination with at least one other antibacterial agent.

10. The method of claim 9, wherein the at least one other antibacterial agent is lysozyme, protamine, a chelating agent, a cupric compound, or a bacteriocin.

11. A method of treating bacterial infection in mammals, including humans, comprising administering a therapeutically effective amount of a protein fraction isolated from dissociated plant chromatin to a mammal in need thereof, wherein the protein fraction has an apparent molecular weight between 10 and 20 kilodaltons (kD), and wherein the bacterial infections are caused by Gram-positive bacteria or Gram-negative bacteria.

12. The method of claim 1, wherein the dissociated plant chromatin is from wheat.

* * * * *